(12) United States Patent
Hutto et al.

(10) Patent No.: US 8,794,050 B2
(45) Date of Patent: Aug. 5, 2014

(54) FLUID SAMPLE ANALYSIS SYSTEMS

(75) Inventors: Kevin W. Hutto, Kuna, ID (US); Swarnal Borthakur, Boise, ID (US)

(73) Assignee: Nanoscopia (Cayman), Inc., Grand Cayman (KY)

( * ) Notice: Subject to any disclaimer, the term of this patent is extended or adjusted under 35 U.S.C. 154(b) by 542 days.

(21) Appl. No.: 13/105,232

(22) Filed: May 11, 2011

(65) Prior Publication Data

US 2012/0194669 A1     Aug. 2, 2012

Related U.S. Application Data

(60) Provisional application No. 61/436,938, filed on Jan. 27, 2011.

(51) Int. Cl.
*G01N 11/00*     (2006.01)

(52) U.S. Cl.
USPC .......................................... 73/53.01

(58) Field of Classification Search
USPC .............................................. 73/53.01
See application file for complete search history.

(56) References Cited

U.S. PATENT DOCUMENTS

| | | | |
|---|---|---|---|
| 6,379,929 B1 * | 4/2002 | Burns et al. .................. | 435/91.2 |
| 2002/0081716 A1 | 6/2002 | Yagi | |
| 2002/0168671 A1 * | 11/2002 | Burns et al. ...................... | 435/6 |
| 2002/0172969 A1 * | 11/2002 | Burns et al. ...................... | 435/6 |
| 2011/0311394 A1 | 12/2011 | Worsman et al. | |
| 2012/0045787 A1 | 2/2012 | Boettiger | |

FOREIGN PATENT DOCUMENTS

WO    2012068499    5/2012

OTHER PUBLICATIONS

Cui et al., "Lensless high-resolution on-chip optofluidic microscopes for *Caenorhabditis elegans* and cell imaging" [online], May 2008 [retrieved on May 11, 2011]. Retrieved from the Internet: http://www.biophot.caltech.edu/publications/pdf/2008-OFM-PNAS.pdf.

Cui et al., "Quantitative differential interference contrast microscopy based on structured-aperture interference" [online], Sep. 2008 [retrieved on May 11, 2011]. Retrieved from the Internet: http://www.biophot.caltech.edu/publications/pdf/Cui-APL-2007-DIC.pdf.

Wu et al., "The application of Fresnel zone plate based projection in optofluidic microscopy" [online], Sep. 2008 [retrieved on May 11, 2011]. Retrieved from the Internet: http://www.biophot.caltech.edu/publications/pdf/Wu-OE-2008-Fresnel.pdf.

\* cited by examiner

*Primary Examiner* — Hezron E Williams
*Assistant Examiner* — Rodney T Frank

(57) ABSTRACT

A fluid sample analyzing system may be formed from an image sensor integrated circuit substrate. A glass wafer may be used to cover a wafer of image sensors. The glass wafer and the image sensor wafer may be attached using oxide bonding. Fluid channels may be formed in a layer that is interposed between the image sensor wafer and the glass wafer. The layer may be deposited on the image sensor wafer and the glass wafer prior to oxide bonding. A spacer may be used to deliver the fluid channel layer to the image sensor wafer before the glass wafer is bonded to the image sensor wafer. The spacer may be formed from a silicon wafer. The silicon wafer may be bonded to the image sensor wafer and thinned, leaving a thin spacer wafer layer on the image sensor wafer in which fluid channels may be formed.

18 Claims, 12 Drawing Sheets

US 8,794,050 B2

FLUID SAMPLE ANALYSIS SYSTEMS

This application claims the benefit of provisional patent application No. 61/436,938, filed Jan. 27, 2011, which is hereby incorporated by reference herein in its entirety.

BACKGROUND

This relates generally to sample analysis systems, and, more particularly, to systems that analyze fluid samples.

Fluid sample analysis systems may be used to analyze fluids containing DNA, cells, and other samples. In these systems, patterns of fluid channels may be used to route fluid to processing regions and imaging regions.

One type of sample analysis system, which is sometimes referred to as an optofluidic microscope, can be used to generate images of cells and other biological specimens. The specimens are suspended in a fluid. The fluid flows over a set of image sensor pixels in a fluid channel. In one arrangement, the image sensor pixels may be associated with an image sensor pixel array that is masked using a metal layer with a pattern of small holes. In a typical arrangement, the holes and corresponding image sensor pixels are arranged in a diagonal line that crosses the channel. As specimens flow through the channel, image data from the pixels may be acquired and processed to form high-resolution images of the specimens.

DETAILED DESCRIPTION

Figure 1:
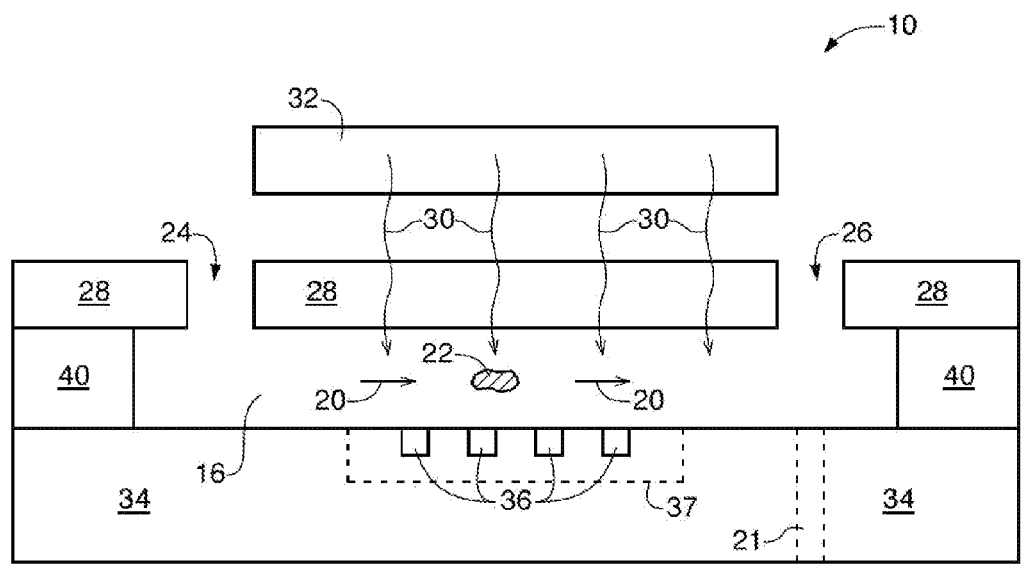
FIG. 1 is a diagram of an illustrative system for imaging and processing cells and other samples in accordance with an embodiment of the present invention.

A cross-sectional side view of an illustrative fluid sample analysis system is shown in FIG. 1. In general, fluid analysis systems such as system 10 may be systems for analyzing DNA, systems for analyzing cells or other biological specimens, or systems for analyzing any other suitable fluid-based samples. Systems such as system 10 may be, for example, optofluidic microscopes.

As shown in FIG. 1, system 10 may include an image sensor integrated circuit such as image sensor integrated circuit 34. Image sensor integrated circuit 34 may be formed from a semiconductor substrate material such as silicon and may contain numerous image sensor pixels 36. Image sensor pixels 36 may form part of an array of image sensor pixels on image sensor integrated circuit 34 and may be controlled by circuitry 37. Some of the pixels may be actively used for gathering light. Other pixels may be inactive or may be omitted from the array during fabrication. In arrays in which fabricated pixels are to remain inactive, the inactive pixels may be covered with metal or other opaque materials, may be depowered, or may otherwise be inactivated. There may be any suitable number of pixels fabricated in integrated circuit 34 (e.g., tens, hundreds, thousands, millions, etc.). The number of active pixels in integrated circuit 34 may be tens, hundreds, thousands, or more).

Image sensor integrated circuit 34 may be covered with a transparent layer of material such as glass layer 28 or other clear covering layers. Sidewalls 40, glass layer 28, and substrate 34 form one or more channels such as channels 16. Channels 16 may have lateral dimensions (dimensions parallel to dimensions x and z in the example of FIG. 1) of a millimeter or less (as an example). The length of each channel (the dimension of channel 16 along dimension y in the example of FIG. 1) may be 1-10 mm, less than 10 mm, more than 10 mm, or other suitable length. Through-silicon vias such as via 21 may be formed to convey signals from image sensor pixels 36 on the front side of image sensor 34 to pads (e.g., a redistribution layer) and solder balls on the back side of the image sensor to facilitate packaging.

During operation, fluid flows through channel 16 as illustrated by arrows 20. A fluid source may be used to introduce fluid into channel 16 through entrance port 24. Fluid may, for example, be dispensed from a pipette, from a drop on top of port 24, from a fluid-filled reservoir, from tubing that is coupled to an external pump, etc. Fluid may exit channel 16 through exit port 26.

The rate at which fluid flows through channel 16 may be controlled using fluid flow rate control structures. Examples of fluid flow rate control structures that may be used in system 10 include pumps, electrodes, microelectromechanical systems (MEMS) devices, etc.

Fluid 20 may contain cells such as cell 22 or other biological elements or particles. As cells such as cells 22 pass by sensor pixels 36, image data may be acquired. In effect, the cell is "scanned" across the pattern of sensor pixels 36 in channel 16 in much the same way that a printed image is scanned in a fax machine. Control circuitry that is implemented as external circuitry or as circuitry that is embedded within image sensor integrated circuit 34 may be used to process the image data that is acquired using sensor pixels 36. Because the size of each image sensor pixel 36 is typically small (e.g., on the order of 0.9-3 microns or less in width), precise image data may be acquired. This allows high-resolution images of cells such as cell 22 to be produced. A typical cell may have dimensions on the order of 1-10 microns (as an example). Images of other samples (e.g., other biological specimens) may also be acquired in this way.

During processing and analysis operations, on-chip and/or off-chip control circuitry may be used to control the operation of light source 32. Light source 32 may be based on one or more lamps, light-emitting diodes, lasers, or other sources of light. Light source 32 may be a white light source or may contain one or more light-generating elements that emit different colors of light. For example, light-source 32 may contain multiple light-emitting diodes of different colors or may contain white-light light-emitting diodes or other white light sources that are provided with different respective colored filters. In response to control signals from control circuitry 42, light source 32 may produce light 30 of a desired color and intensity. Light 30 may pass through glass layer 28 to illuminate the sample in channel 16 (e.g., to acquire images, to make fluorescence measurements, etc.). If desired, the fluid sample in channel 16 may be heated, exposed to electrical signals, or exposed to light 30 (e.g., laser light) to process the sample. In analysis and processing systems with samples other than cells (e.g., DNA samples), other types of processing and analysis operations may be performed (e.g., repeated heating and cooling cycles, etc.). The use of an optofluidic microscope analysis system in the FIG. 1 example is merely illustrative.

Conventional fluid channels in optofluidic microscopes include polymer surfaces. For proper operation of an optofluidic microscope, it may be desirable to have hydrophilic channels. Conventional polymer channel surfaces may be rendered hydrophilic by incorporating additives into the polymer materials that are used in forming the fluid channels, but the resulting hydrophilic behavior is typically not permanent. Conventional polymer channel surfaces are also prone to absorbing organic materials from samples, may be susceptible to damage by saline solutions, and may be limited in their ability to handle desired pressures and temperatures.

To address these shortcomings, fluid channel 16 of system 10 may be constructed using materials such as glass, silicon, nitride, oxide, or other materials that are strong, temperature resistant and hydrophilic. With one suitable arrangement, a glass layer may be attached to an imager wafer that contains oxide fluid channels. With another suitable arrangement, fluid channels may be created in a spacer that is bonded between a glass layer and an imager wafer using an oxide bonding process.

By eliminating polymers from the fluid channels, the need for special additives or additional process steps to create a hydrophilic surface may be avoided. Organic material absorption into the channels may be prevented and the risk of swelling may be reduced. fluid channels in accordance with embodiments of the invention may be hydrophilic, rigid, and capable of handling high temperatures and pressures. The distance between the upper surface of layer 28 and channel 16 can be minimized, because it may be possible to create sidewalls 40 with relatively small heights (in dimension Z of FIG. 1) compared to conventional polymer sidewall structures. Conventional sidewalls may have thicknesses of about 40 microns, which may cause a small cell (e.g., a 1 micron cell) to be out of focus during imaging operations. With embodiments of the present invention, sidewall height in dimension z may be reduced (e.g. to less than 10 microns, less than 5 microns, less than 3 microns, or less than 2 microns, in the range of 0.5 to 5 microns, etc.), allowing for sharper images. Short z-heights may also allow laser light 30 from source 32 to be accurately focused onto a sample (e.g., by a lens that is formed from part of glass layer 28 or an external lens).

Figure 2:
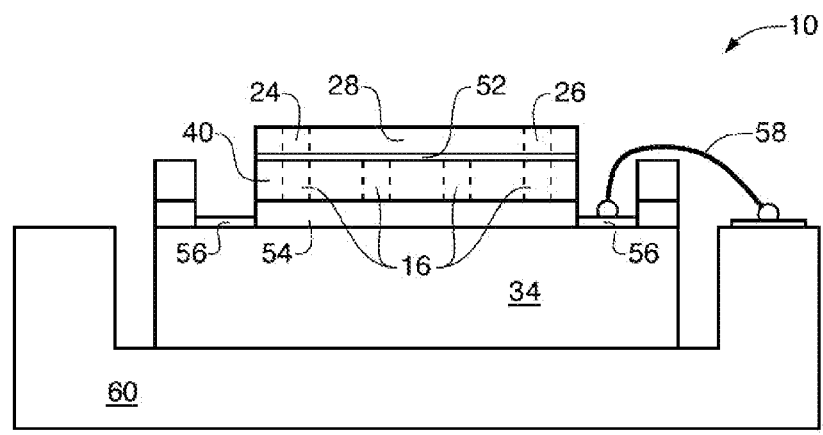
FIG. 2 is a cross-sectional side view of an illustrative system in which an imager has been electrically connected to a package using wire bonds in accordance with an embodiment of the present invention.

If desired, system 10 may be formed by packaging an image sensor with fluid channels into a package and forming bond wire connections between the image sensor and the package. This type of arrangement is shown in FIG. 2. As shown in FIG. 2, image sensor integrated circuit 34 may have a silicon nitride ("nitride") passivation layer 54 that is patterned to expose bond pads 56. Layer 40 may be formed from silicon oxide.

The silicon oxide may be deposited using chemical vapor deposition (CVD) and polished using chemical mechanical polishing (CMP) techniques before attaching glass layer 28 with adhesive 52 or other bonding layers. CVD oxide 40 may be patterned to form channels such as channels 16, some of which may be aligned with openings such as openings 24 and 26. The thickness of CVD oxide 40 may be about 0.5 to 5 microns (as an example) or may be less than 5 microns or more than 5 microns if desired. Spin-on-glass, other spin-on-dielectrics, and other layers of materials maybe used in forming layer 40 if desired. Following dicing into individual die (singulation), glass layer 28 may be attached, imager 34 may be mounted in package 60, and wire bonds 58 may be formed using a wire bonding tool.

Figure 3:
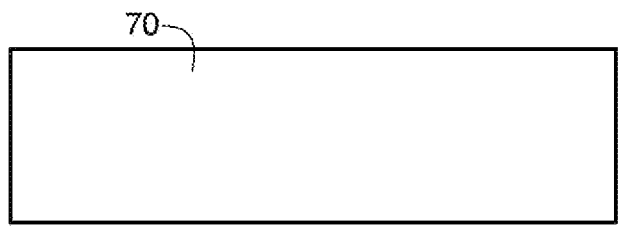
FIG. 3 is a cross-sectional side view of an illustrative glass wafer prior to coating in accordance with an embodiment of the present invention.
Figure 4:
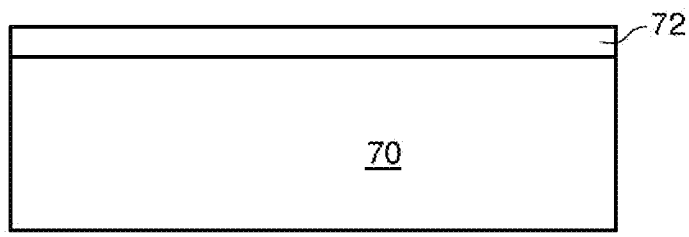
FIG. 4 is a cross-sectional side view of an illustrative glass wafer after coating with an oxide layer in accordance with an embodiment of the present invention.

Wafer-scale processing may be desirable to improve manufacturability. An illustrative wafer-scale process for forming system 10 involves bonding a glass wafer to a wafer of image sensors 34. Initially, a glass wafer such as wafer 70 of FIG. 3 may be prepared for subsequent processing (e.g., by cleaning with a solvent). An optional oxide layer such as a CVD layer of silicon oxide may be deposited on glass wafer 70, as shown by silicon oxide layer 72 of FIG. 4. Layer 72 may be about 0.5 to 10 microns thick or may be less than 10 microns or more than 10 microns. Wafer 70 may be about 400 to 500 microns thick or may have other suitable thicknesses. An illustrative glass that may be used to form wafer 70 may be borosilicate glass. Other types of glass may be used if desired.

Figure 5:
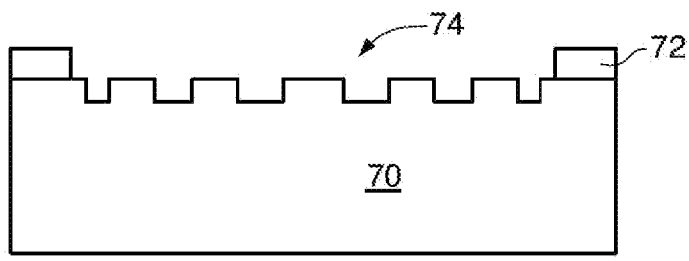
FIG. 5 is a cross-sectional side view of an illustrative glass wafer in which a Fresnel lens has been formed by etching in accordance with an embodiment of the present invention.
Figure 6:
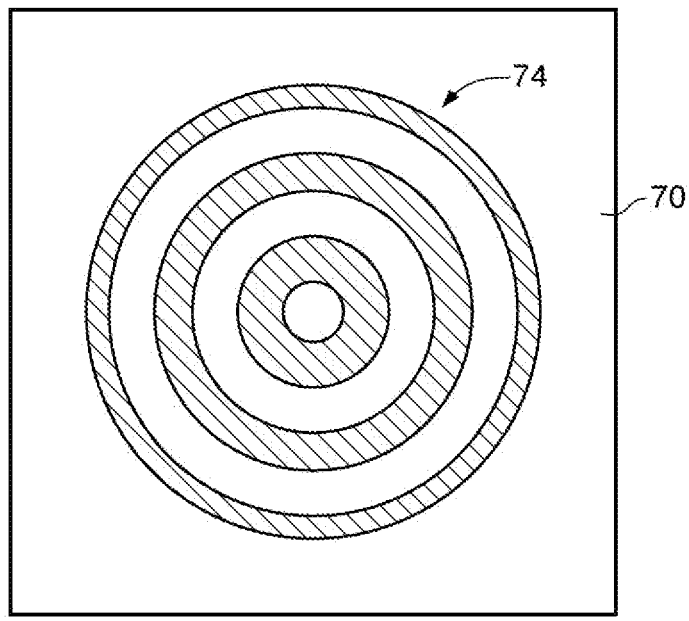
FIG. 6 is a top view of an illustrative Fresnel lens etched into a glass wafer in accordance with an embodiment of the present invention.

As shown in FIG. 5, glass 70 may be patterned (e.g., using wet and/or dry etching) and a portion of the CVD layer may be opened to create a lens such as Fresnel lens 74. Fresnel lens 74 may be used to concentrate light from light source 32 onto material in an associated channel 16. Fresnel lenses such as Fresnel lens 74 of FIG. 5 may be formed on the upper surface of glass wafer 70 (i.e., on the side opposite the underlying fluid channels in system 10) or may be formed on the lower surface of glass wafer 70 (i.e., on the side of the glass wafer that is facing the fluid channels in system 10). A top view of an illustrative Fresnel lens 74 that has been created in wafer 70 is shown in FIG. 6. During wafer-level processing, numerous lenses such as lens 74 of FIG. 6 may be created across wafer 70. Each lens may focus on one or many pixels depending on the pixel size and lens size. Only a single lens is shown in FIGS. 5 and 6 to avoid over-complicating the drawing.

Figure 7A:
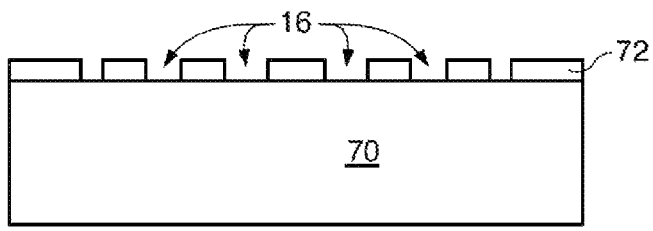
FIG. 7A is a cross-sectional side view of an illustrative glass wafer having a layer of oxide that has been patterned to incorporate features such as fluid channels or portions of a Fresnel lens in accordance with an embodiment of the present invention.
Figure 7B:
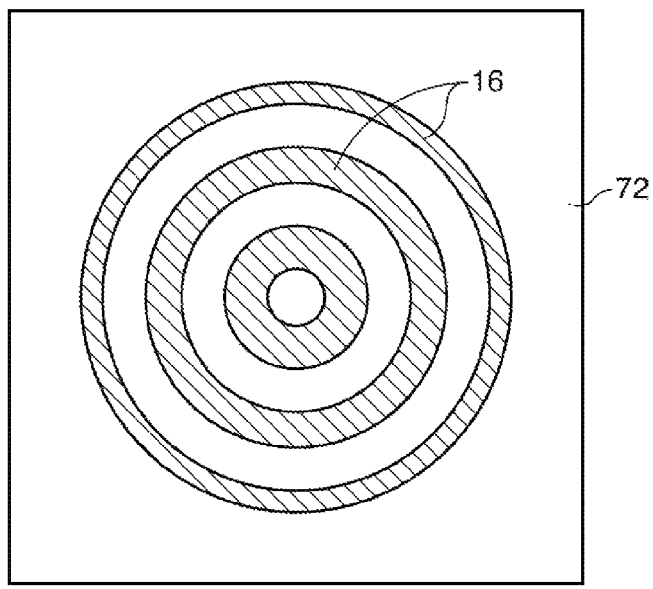
FIG. 7B is a top view of an illustrative Fresnel lens that has been formed by patterning a layer of oxide in accordance with an embodiment of the present invention.
Figure 7C:
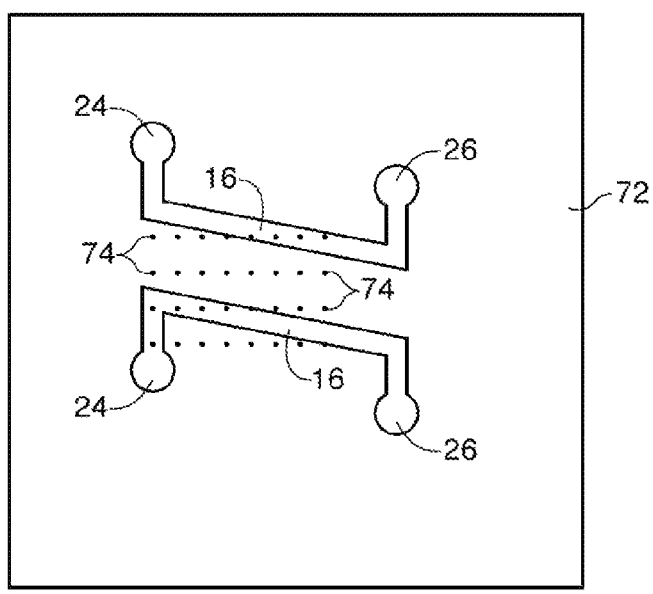
FIG. 7C is a top view of an illustrative channel pattern that has been formed from a patterned oxide layer in accordance with an embodiment of the present invention.

The cross-sectional side view of FIG. 7A and the top view of FIG. 7C show how fluid channels 16 may, if desired, be etched into oxide coating 72. Any suitable pattern of channels 16 may be formed (e.g., patterns with straight channels, curved channels, branching channels, etc.). FIG. 7B is a top view of an illustrative Fresnel lens formed from patterned oxide 72. If desired, Fresnel lenses may be formed in an array on wafer 70 (e.g., in an array having multiple rows and columns) and channels 16 may be oriented at an angle with respect to the rows, thereby causing a given channel 16 to gradually cross over a row of Fresnel lenses. Fresnel lenses may, for example, be located so that their centers are aligned with the array of dots 74 of FIG. 7C.

Fluid channels may, in general, be formed 1) entirely in oxide 72 on glass wafer 70, 2) entirely in oxide coating 40 of image sensor wafer 34, or 3) partly in oxide 72 on glass wafer 70 and partly in oxide 40 of image sensor wafer 34. Each of these options may be used in combination with a) Fresnel lenses formed in glass 70, b) Fresnel lenses formed in oxide 72 on glass 70, or c) glass and oxide without Fresnel lenses.

After patterning channels 16, lenses 74 and/or other desired features on wafer 70, wafer 70 can be bonded to an imager wafer using oxide bonding. During oxide bonding, wafer 70 is placed in contact with the imager wafer. Van der Waals forces hold the wafer in place on the imager wafer. Heat is then applied (e.g., at about 250° C. to 300° C. for one hour), forming a completed oxide bond. The presence of oxide coating 72 on glass wafer 70 may help promote adhesion between wafer 70 and the wafer of imagers 34 during oxide bonding.

Figure 8:
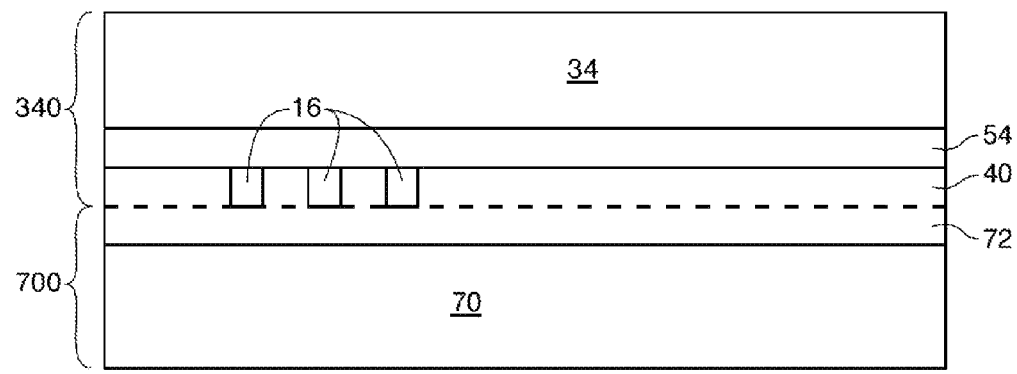
FIG. 8 is a cross-sectional side view of a fluid sample analysis system formed from an image wafer having a layer of nitride passivation and a layer of patterned oxide including fluid channels that has been oxide bonded to an image sensor wafer in accordance with an embodiment of the present invention.

FIG. 8 is a cross-sectional side view of an illustrative system following attachment of image sensor wafer 34 to glass wafer 700. As shown in FIG. 8, glass wafer 700 may include a glass wafer substrate such as glass wafer 70 and an oxide coating such as coating 72. Oxide coating 72 and the other oxides described herein may be silicon oxides, titanium oxides, hafnium oxides, other metal oxides, etc.

Image sensor wafer 340 my include image sensor wafer 34, a nitride coating layer 54, and a layer of oxide (e.g., oxide 40) in which channels 16 have been formed. Following oxide bonding of the image sensor wafer and the glass wafer, channels 16 have upper and lower surfaces and left and right sidewalls formed from oxide.

Figure 9:
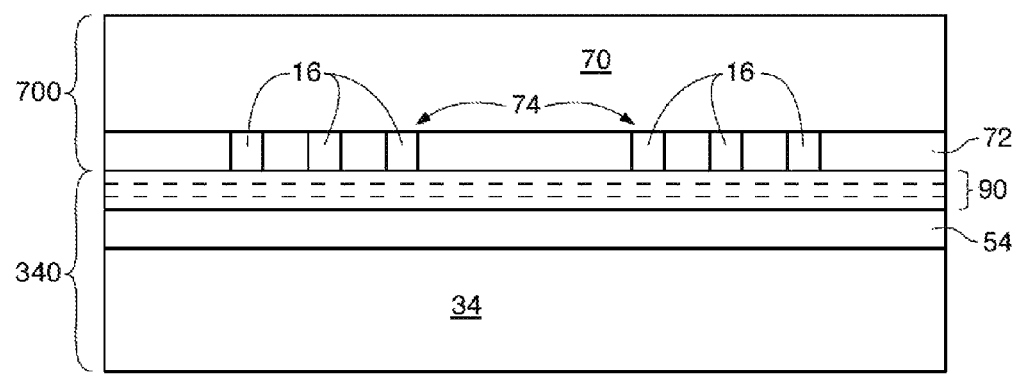
FIG. 9 is a cross-sectional side view of a fluid sample analysis system formed from an image sensor wafer that is coated with interference filter layers in accordance with an embodiment of the present invention.
Figure 10:
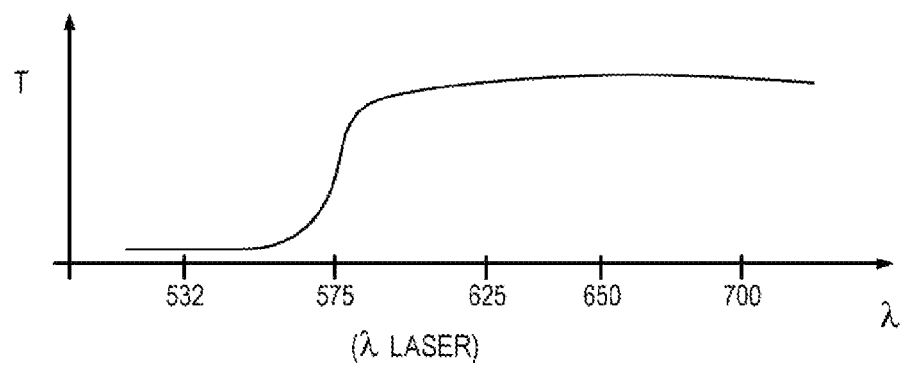
FIG. 10 is a graph illustrating a transmission spectrum that may be produced by the interference layers in the fluid sample analysis system of FIG. 9 in accordance with an embodiment of the present invention.

If desired, an optical filter may be formed in the fluid sample analysis systems. An illustrative configuration of the type that may include a filter is shown in FIG. 9. As shown in FIG. 9, image sensor wafer 340 and glass wafer 700 may be combined using oxide bonding. Glass wafer 700 may include glass wafer substrate 70 with oxide coating 72. Lenses such as Fresnel lenses 74 may be etched into glass 70. Fluid channels such as channels 16 may be formed in oxide layer 72. Image sensor wafer 340 may include image sensor substrate wafer 34 and coating layers. Wafer 34 may, for example, be coated with a passivation layer such as silicon nitride layer 54. Layers 90 may be used to form an optical filter. Layers 90 may, for example, be formed from a stack of multiple dielectric layers having alternating high and low indices of refraction. For example, layers 90 may include alternating layers of silicon oxide (or titanium oxide, hafnium oxide, or other oxides) and layers of silicon nitride or other dielectric materials. There may be, for example, three or more, four or more, or five or more alternating layers of oxide and nitride, ending in a layer of oxide as the top layer to promote adhesion during oxide bonding. The high-low stack that is formed in this way may serve as an interference filter (e.g., a bandpass filter, notch filter, etc.). FIG. 10 shows how layers 90 may be configured to implement a bandpass filter having a pass band starting above about 575 nm. This type of filter may be used to block laser light at about 532 nm (as an example), while allowing light above 575 nm to pass through the filter. This type of filter may therefore be used to observe DNA fluorescence emissions at greater than 532 nm. Filters with other pass bands may be used if desired. The example of FIG. 10 is merely illustrative.

Figure 11:
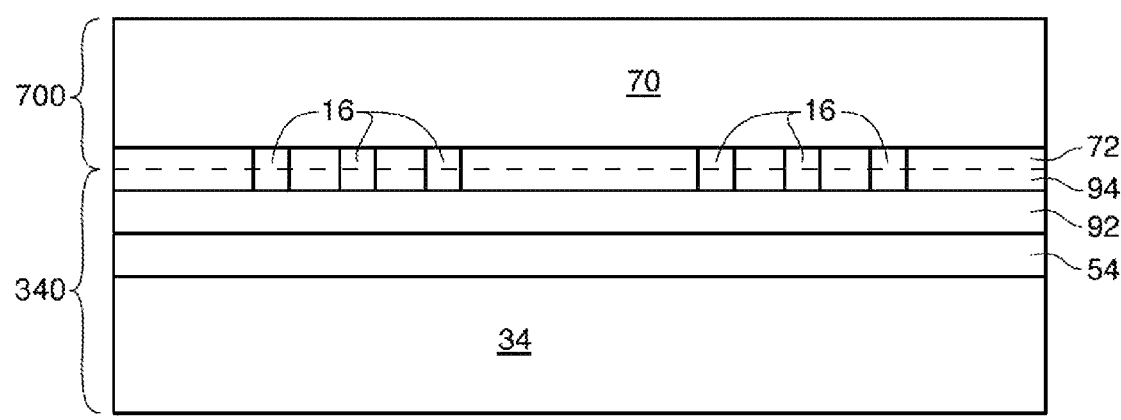
FIG. 11 is a cross-sectional side view of an illustrative fluid sample analysis system having an absorption filter layer in accordance with an embodiment of the present invention.

FIG. 11 shows how a filter may be implemented using a polymer or other material that serves as an absorption filter. Glass wafer 700 may include glass wafer substrate 70 coated with a layer of oxide 72. Image sensor wafer 340 may include image sensor wafer 34 and coating layers such as nitride passivation layer 54, filter layer 92, and oxide layer 94. Oxide layer 94 and/or oxide layer 72 may be patterned to form channels 16 and may be bonded together using oxide bonding. Filter layer 92 may be formed from a polymer or other material that absorbs light in a desired range of wavelengths. Oxide layer 94 may be deposited on top of layer 92 using CVD, spin-on processes, or other deposition techniques, thereby forming an oxide cap layer suitable for oxide bonding with glass wafer 700.

Figure 16:
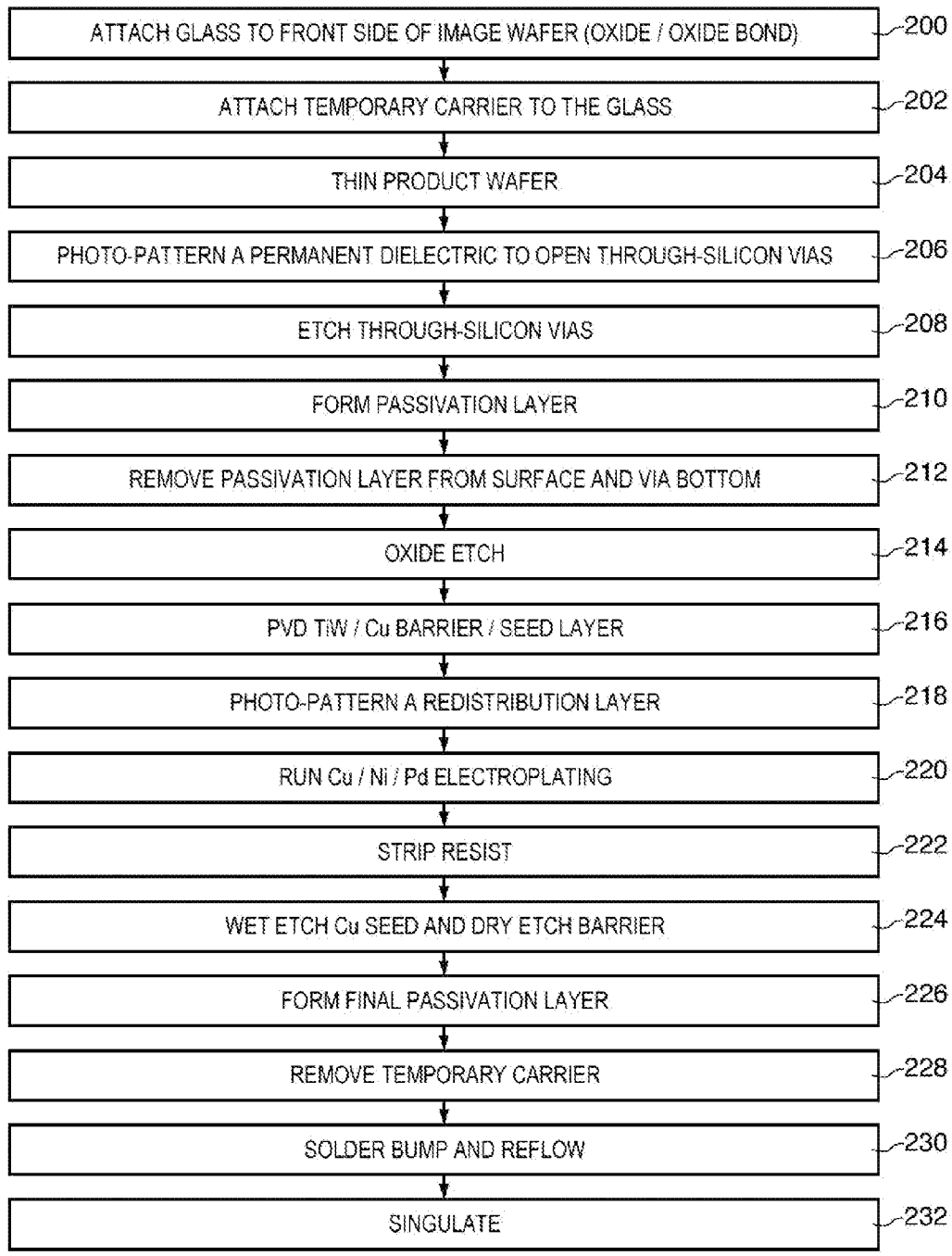
FIG. 16 is a flow chart of an illustrative glass-first process that may be used in forming a fluid sample analysis system in accordance with an embodiment of the present invention.
Figure 17:
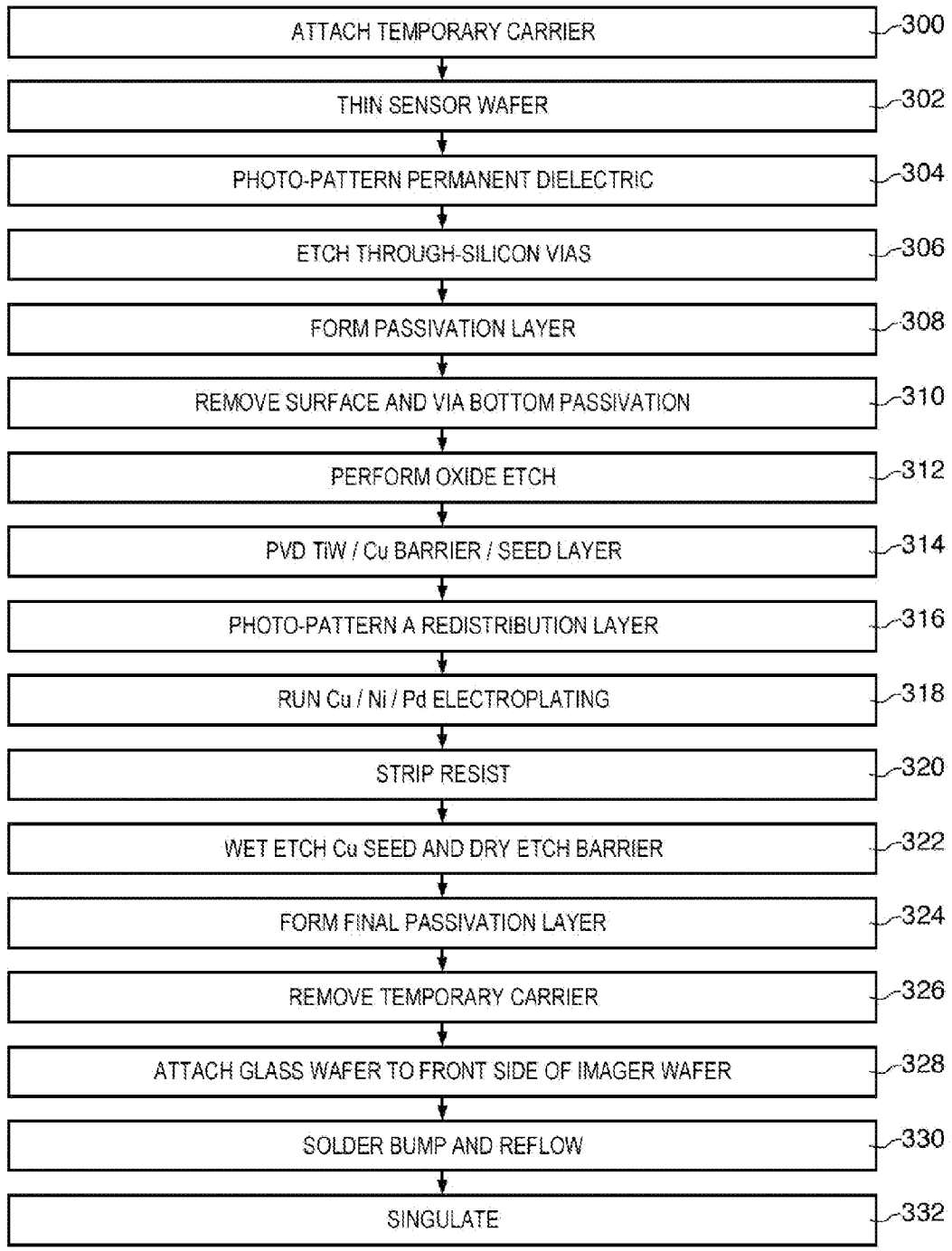
FIG. 17 is a flow chart of an illustrative glass-last process that may be used in forming a fluid sample analysis system in accordance with an embodiment of the present invention.

Illustrative process flows are shown in FIGS. 16 and 17. With these illustrative processes, the glass wafer is oxide bonded to the imager wafer. Through-silicon-vias may be formed through the silicon die that makes up the imager wafer and a redistribution layer (RDL) with solder balls may be formed on the back of the imager wafer.

The steps of FIG. 16 corresponds to a glass-first process. With this type of process an oxide bond is formed with the glass wafer first. Holes 24 and 26 are present in the glass wafer before attachment to the image sensor wafer. A temporary spacer (carrier) is used on the glass side to protect the holes prior to the through-silicon via formation process.

The glass first process starts with step 200. At step 200, glass wafer 70 (with holes) is attached to the front side of the image sensor wafer using oxide bonding.

At step 202, the temporary carrier is attached to the glass.

At step 204, the image sensor wafer is thinned to about 100 microns in thickness. The thinning process may involve polishing using a coarse grind, a fine grind, and a chemical mechanical polishing (CMP) operation, dry polish, or plasma polish.

At step 206, photo-patterning techniques may be used to open holes in a permanent dielectric that serves as a patterned etch mask for forming the through-silicon vias.

At step 208, the through-silicon vias may be etched (e.g., using a Bosch silicon deep via etch).

At step 210, a sidewall passivation layer may be formed by spin-coating a polymer layer that conformally coats the surface, via sidewalls, and via bottoms. If desired, CVD oxide or other passivation layers may be formed.

At step 212, the passivation layer may be removed from the surface and the via bottom using a blanket dry etch. The via sidewalls are untouched because the blanket dry etch is a directional etch.

At step 214, an oxide etch is performed to expose an aluminum bond pad at the via bottom.

At step 216, a physical vapor deposition process is performed to deposit a barrier/seed layer (e.g., using TiW/Cu). Other barrier options include Ta, TaN, Ti, etc.

At step 218, a redistribution layer (RDL) may be patterned on the rear surface of the imager wafer.

At step 220, an electroplating process may be performed (e.g., using Cu/Ni/Pd electroplating).

At step 222, photoresist is stripped.

At step 224, a wet etch is performed on the Cu seed layer and the barrier is dry etched.

At step 226, a final passivation layer (i.e., a solder mask) may be deposited by laminating a dry film solder mask material or by spin-coating or spray coating the solder mask.

At step 228, the temporary carrier is removed from the glass wafer.

At step 230, solder bump and reflow operations may be performed.

At step 232, the wafer may be singulated and individual fluid sample analysis systems may be packaged.

The illustrative process of FIG. 17 is a glass last process. With the FIG. 17 approach, the image sensor wafer is bonded to a temporary carrier before running the through-silicon via process. After the redistribution layer on the back side of the image sensor wafer has been formed, the temporary carrier may be removed. The glass wafer is then attached with holes.

With the glass last process, the temporary carrier is attached to the image sensor wafer at step 300.

At step 302, the image sensor wafer is thinned to about 100 microns in thickness. The thinning process may involve polishing using a coarse grind, a fine grind, and a chemical mechanical polishing (CMP) operation, dry polish, or plasma polish.

At step 304, photo-patterning techniques may be used to open holes in a permanent dielectric that serves as a patterned etch mask for forming the through-silicon vias.

At step 306, the through-silicon vias may be etched (e.g., using a Bosch silicon deep via etch).

At step 308, a sidewall passivation layer may be formed by spin-coating a polymer layer that conformally coats the surface, via sidewalls, and via bottoms. If desired, CVD oxide or other passivation layers may be formed.

At step 310, the passivation layer may be removed from the surface and the via bottom using a blanket dry etch. The via sidewalls are untouched because the blanket dry etch is a directional etch.

At step 312, an oxide etch is performed to expose an aluminum bond pad at the via bottom.

At step 314, a physical vapor deposition process is performed to deposit a barrier/seed layer (e.g., using TiW/Cu). Other barrier options include Ta, TaN, Ti, etc.

At step 316, a redistribution layer (RDL) may be patterned on the rear surface of the imager wafer.

At step 318, an electroplating process may be performed (e.g., using Cu/Ni/Pd electroplating).

At step 320, photoresist is stripped.

At step 322, a wet etch is performed on the Cu seed layer and the barrier is dry etched.

At step 324, a final passivation layer (i.e., a solder mask) may be deposited by laminating a dry film solder mask material or by spin-coating or spray coating the solder mask.

At step 326, the temporary carrier is removed from the sensor wafer.

At step 328, the glass wafer is attached to the front side of the imager wafer.

At step 330, solder bump and reflow operations may be performed.

At step 332, the wafer may be singulated and individual fluid sample analysis systems may be packaged.

Figure 18:
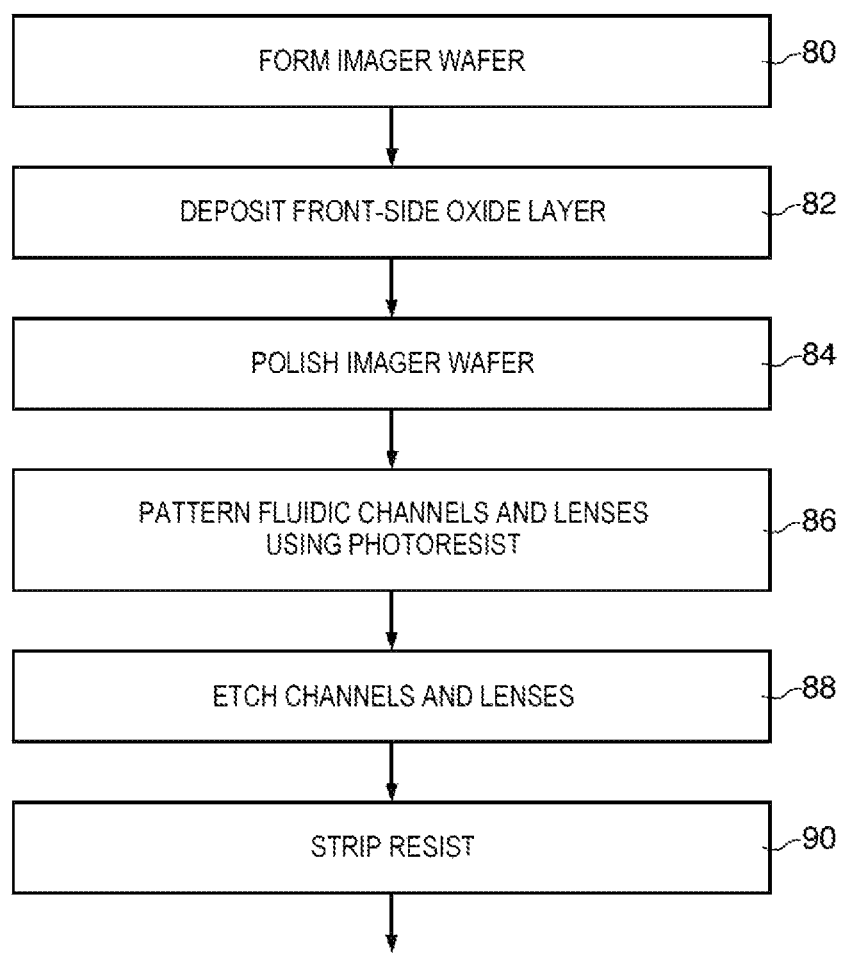
FIG. 18 is a flow chart of illustrative steps involved in preparing an image sensor wafer for assembly into a fluid sample analysis system in accordance with an embodiment of the present invention.

Illustrative steps that may be used to prepare the imager wafer prior to forming the fluid sample analysis system using processes of the type shown in FIGS. 16 and 17 are shown in FIG. 18.

At step 80, a wafer of imagers 34 is fabricated using semiconductor processing tools. The wafer is preferably coated with a silicon nitride passivation layer and an optional silicon oxide coating layer (or other oxide coating such as a metal oxide coating, etc.).

At step 82, a front-side oxide layer is deposited on the imager wafer (e.g., using CVD, a spin-on process, etc.).

At step 84, the imager wafer may be polished (e.g., using a CMP process).

At step 86, photolithography may be used to pattern a layer of photoresist on the surface of the imager wafer. For example, photoresist may be patterned to define a desired pattern for fluid channels 16 in the oxide layer on the imager wafer and/or a pattern form forming Fresnel lenses. Channels 16 and lenses 74 may then be etched into the oxide layer at step 88. The photoresist may be stripped and the wafer cleaned at step 90. Steps 86, 88, and 90 may be skipped in scenarios in which channels 16 are being formed on the glass wafer (e.g., in oxide layer 72).

Figure 19:
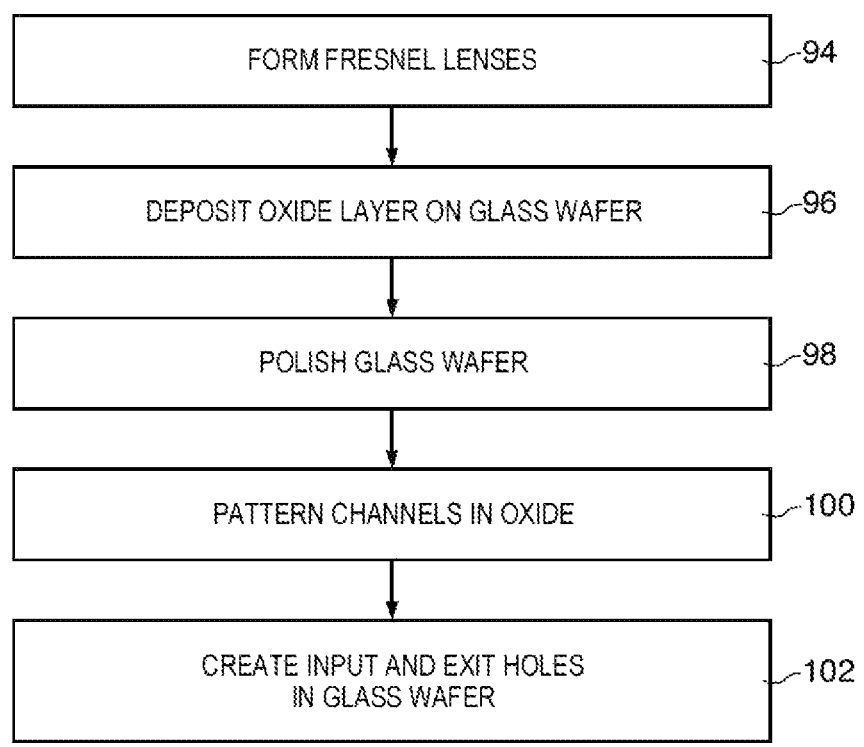
FIG. 19 is a flow chart of illustrative steps involved in preparing a glass wafer for assembly into a fluid sample analysis system in accordance with an embodiment of the present invention.

Illustrative steps involved in preparing a glass wafer prior to forming the fluid sample analysis system using processes of the type shown in FIGS. 16 and 17 are shown in FIG. 19.

At step 94, optional Fresnel lenses 74 may be formed in the glass wafer.

At step 96, oxide layer 72 may be formed on glass wafer 70 (if desired, some oxide may be deposited on glass wafer 70 and some of the oxide may be deposited on the imager wafer to reduce the thermal exposure of the glass wafer and imager wafer).

At step 98, the glass wafer may be polished (e.g., to help ensure maximum planarity and a corresponding satisfactory oxide bond).

At step 100, channels 16 may, if desired, be formed in the oxide layer on the glass wafer (e.g., by wet and/or dry etching).

At step 102, openings for channel inputs and outputs such as entrance opening 24 and exit 26 of FIG. 1 may be formed in the glass wafer.

Following preparation of the image sensor wafer using operations of the type shown in FIG. 18 and preparation of the glass wafer using operations of the type shown in FIG. 19, a glass first process of the type shown in FIG. 16 or a glass last process of the type shown in FIG. 17 may be used in assembling the image sensor wafer and glass wafer into fluid sample analysis systems.

Figure 20:
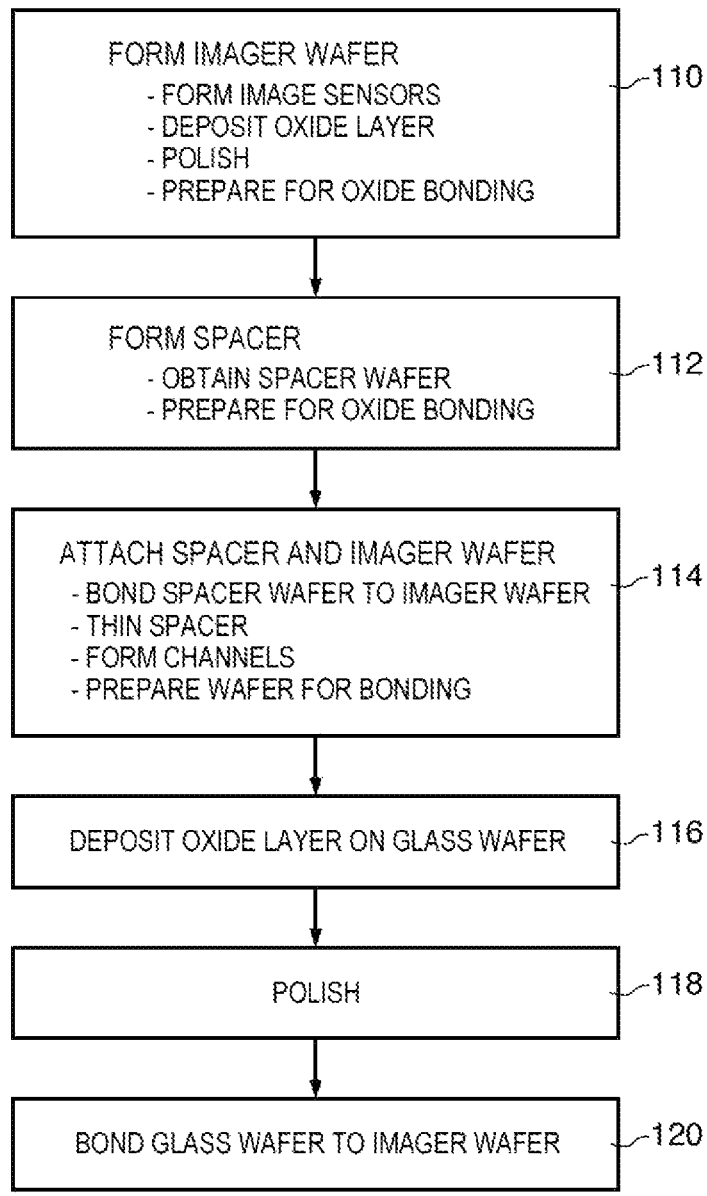
FIG. 20 is a flow chart of illustrative steps involved in forming a fluid sample analysis system using a spacer in accordance with an embodiment of the present invention.

If desired, a fluid sample analysis system with hydrophilic channels may be formed using a spacer such as a silicon spacer. An illustrative process that may be used to form this type of system is shown in FIG. 20.

At step 110, the imager wafer may be formed. The image sensor wafer may initially be provided with a set of image sensors. The image sensors may be coated with an oxide layer. The image sensor wafer with the oxide coating may then be polished to ensure sufficient planarity for forming an oxide bond. The polished wafer may be activated (e.g., using dry and/or wet activation techniques).

At step 112, a spacer wafer may be formed. An example of a suitable spacer wafer is a wafer of silicon having a lightly doped n or p substrate and a corresponding heavily doped n+ or p+ epitaxial layer. If desired, silicon on oxide wafers or other types of spacer wafers may be used if desired. During the operations of step 112, the spacer wafer may be prepared for oxide bonding (e.g., by coating with oxides, by cleaning exposed surfaces, etc.).

Figure 12:
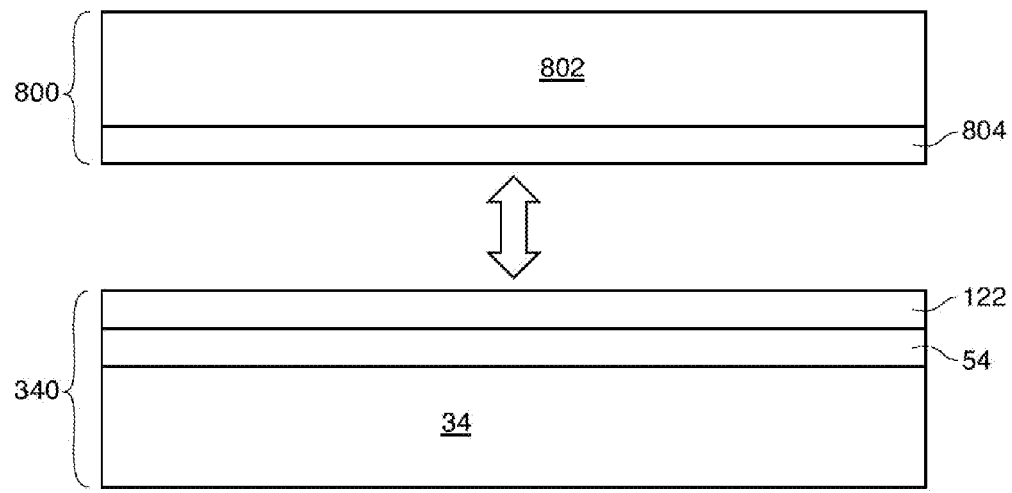
FIG. 12 is a cross-sectional side view of a spacer wafer being bonded to an image sensor wafer in accordance with an embodiment of the present invention.
Figure 13:
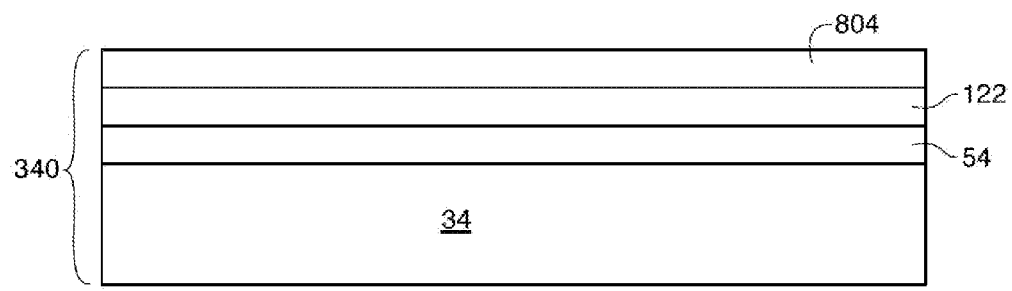
FIG. 13 is a cross-sectional side view of the image sensor wafer of FIG. 12 following attachment and thinning of the spacer wafer to leave a thinned spacer wafer layer on the surface of the image sensor wafer in accordance with an embodiment of the present invention.
Figure 14:
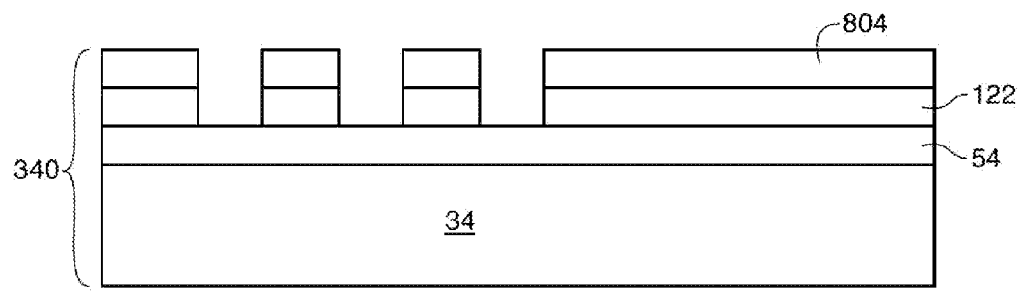
FIG. 14 is a cross-sectional side view of the image sensor wafer and thinned spacer wafer layer of FIG. 13 following formation of fluid channels in accordance with an embodiment of the present invention.
Figure 15:
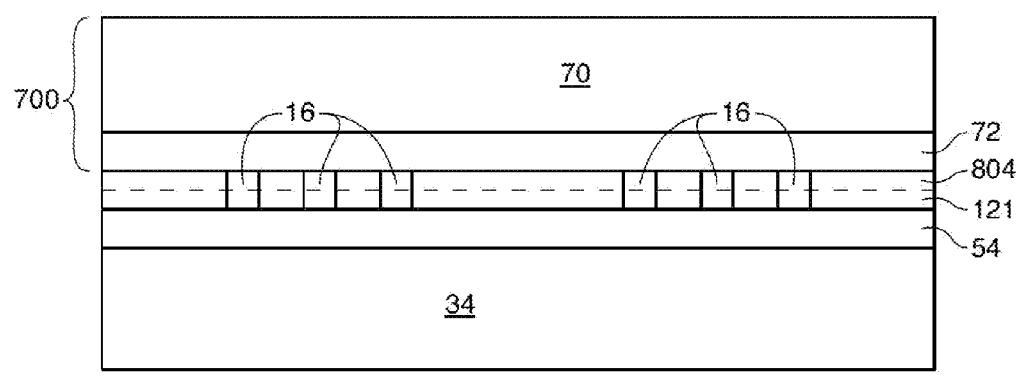
FIG. 15 is a cross-sectional side view of the image sensor wafer of FIG. 14 following oxide bonding of glass wafer to serve as a cover in accordance with an embodiment of the present invention.

At step 114, the spacer and imager wafers may be bonded together using oxide bonding. FIG. 12 is a cross-sectional side view of an image sensor wafer 340 having an image sensor integrated circuit substrate wafer 34, a nitride passivation layer 54, and an oxide coating 122 in the process of being attached to a spacer 800 having a spacer substrate and a coating 804 by oxide bonding. In configurations in which spacer 802 is formed from silicon with an oxide layer, layer 804 is formed from pure oxide. In configurations in which wafer 802 is a silicon-on-oxide (SOI) wafer, coating 804 may be made up of an oxide layer and a silicon layer. In configurations in which spacer 802 is a silicon epitaxial wafer, coating 804 may be made up of a silicon epi layer. Following bonding of spacer 800 and image sensor wafer 340 of FIG. 12, spacer layer 802 may be thinned using CMP processes. In epi silicon wafer embodiments, a wet etch may be performed to remove residual silicon from wafer 802. Following thinning during the operations of step 114, image sensor wafer 340 may appear as shown in FIG. 13 (i.e., covered with layer 804 from spacer 800). Channels 16 may then be formed in layers 804 and 122 using wet and/or dry etching processes and image sensor wafer 340 may be prepared for bonding, following which the image sensor wafer 340 may appear as shown in FIG. 14.

At step 116 of FIG. 20, a glass wafer 70 may be coated with a layer of oxide 72. The oxide may be polished to ensure satisfactory planarity for bonding (step 118). During the operations of step 120, the glass wafer 700 that includes wafer 70 and oxide 72 may, as an example, be oxide bonded to the imager wafer 340 of FIG. 20, following which the wafer will be ready for singulation and further processing. If desired, a glass-first process may be used.

Various embodiments have been described illustrating fluid sample analysis systems. The fluid sample analysis systems may have channels formed from materials such as oxides that are stable at elevated temperatures and pressures and that are hydrophilic. A glass wafer that serves as a cover may be oxide bonded to an image sensor wafer. The image sensor wafer may be coated with an oxide layer to promote oxide bonding. In some embodiments, a spacer such as a silicon wafer may be used to deliver layers to an image sensor wafer. Channels may be formed in the spacer layers and may be covered using a glass wafer.

The foregoing is merely illustrative of the principles of this invention which can be practiced in other embodiments.

What is claimed is:

1. A method for forming a fluid sample analyzing system, comprising:
   forming a wafer of image sensors;
   oxide bonding a glass wafer to the wafer of image sensors; and
   forming Fresnel lenses in the glass wafer before oxide bonding the glass wafer to the wafer of image sensors, wherein the glass wafer has opposing first and second sides, wherein forming the Fresnel lenses comprises forming the Fresnel lenses on the first side, and wherein oxide bonding the glass wafer comprises oxide bonding a selected one of the first and second sides of the glass wafer to the wafer of image sensors.

2. The method defined in claim 1 further comprising:
   forming fluid channels in at least part of the wafer of image sensors before oxide bonding the glass wafer to the wafer of image sensors.

3. The method defined in claim 1 further comprising:
   forming fluid channels in at least part of the glass wafer before oxide bonding the glass wafer to the wafer of image sensors.

4. The method defined in claim 1 further comprising:
   forming fluid channels in at least part of the wafer of image sensors and in at least part of the glass wafer before oxide bonding the glass wafer to the wafer of image sensors.

5. The method defined in claim 1 further comprising depositing an oxide layer on the wafer of image sensors and polishing the oxide layer before oxide bonding the glass wafer to the wafer of image sensors.

6. The method defined in claim 1 further comprising depositing an oxide layer on the glass wafer before oxide bonding the glass wafer to the wafer of image sensors.

7. The method defined in claim 1 wherein the bonded glass wafer and wafer of image sensors forms a wafer that contains fluid channels, the method further comprising:
   depositing a nitride passivation layer over the wafer of image sensors; and
   before oxide bonding the glass wafer to the wafer of image sensors, depositing a layer of oxide on the nitride passivation layer.

8. The method defined in claim 1 wherein the bonded glass wafer and wafer of image sensors forms a wafer that contains fluid channels, the method further comprising:
   incorporating an optical filter layer into the wafer that contains the fluid channels by depositing dielectric layers that form an interference filter.

9. The method defined in claim 1 wherein the bonded glass wafer and wafer of image sensors forms a wafer that contains fluid channels, the method further comprising:
   incorporating an optical filter layer into the wafer that contains the fluid channels by depositing a polymer layer that forms an absorption filter.

10. The method defined in claim 1 further comprising forming a layer of oxide with fluid channels, wherein the layer oxide with fluid channels is interposed between the image sensor wafer and the glass wafer when the glass wafer is oxide bonded to the image sensor wafer.

11. A method for forming a fluid sample analyzing system, comprising:
   forming a wafer of image sensors;
   attaching a spacer wafer to the wafer of image sensors;
   thinning the spacer wafer to form a spacer wafer layer on the wafer of image sensors; and
   attaching a glass wafer to the wafer of image sensors over the spacer wafer layer.

12. The method defined in claim 11 wherein attaching the glass wafer to the wafer of image sensors comprises oxide bonding the glass wafer.

13. The method defined in claim 12 further comprising:

forming an oxide layer on the glass wafer before oxide bonding the glass wafer; and forming fluid channels in the spacer wafer layer.

14. The method defined in claim 13 wherein the spacer wafer layer includes at least one silicon layer, wherein forming the fluid channels comprises forming at least part of the fluid channels in the silicon layer, wherein the spacer wafer layer includes at least one oxide layer, and wherein forming the fluid channel comprises forming at least part of the fluid channels in the oxide layer included in the spacer wafer layer.

15. The method defined in claim 11 further comprising forming Fresnel lenses in the glass wafer, wherein the glass wafer has opposing first and second sides, wherein forming the Fresnel lenses comprises forming the Fresnel lenses on the first side, and wherein attaching the glass wafer comprises attaching a selected one of the first and second sides to the wafer of image sensors.

16. A fluid sample analyzing apparatus, comprising:

an image sensor integrated circuit substrate;

a glass layer that is oxide bonded to the image sensor; and at least one oxide layer that is interposed between the image sensor integrated circuit substrate and the glass layer, wherein the oxide layer includes fluid channels, wherein the glass layer comprises at least one Fresnel lens, wherein the glass wafer has opposing first and second sides, wherein the first side is oxide bonded to the image sensor, and wherein the Fresnel lenses are located on a selected one of the first and second sides.

17. The fluid sample analyzing apparatus defined in claim 16 further comprising at least one silicon layer interposed between the image sensor integrated circuit substrate and the glass layer, wherein the silicon layer includes at least part of the fluid channels.

18. The fluid sample analyzing apparatus defined in claim 16 further comprising at least one filter layer interposed between the fluid channels and the glass layer, wherein the filter layer includes a filter layer selected from the group consisting of: an absorption filter layer and an interference filter layer.

* * * * *